United States Patent
Ohtsuka

Patent Number: 5,237,356
Date of Patent: Aug. 17, 1993

[54] FUNDUS CAMERA PHOTOGRAPHIC OPTICAL SYSTEM

[75] Inventor: Hiroyuki Ohtsuka, Tokyo, Japan

[73] Assignee: Kabushiki Kaisha Topcon, Tokyo, Japan

[21] Appl. No.: 868,396

[22] Filed: Apr. 14, 1992

[30] Foreign Application Priority Data

Apr. 15, 1991 [JP] Japan .................. 3-082658

[51] Int. Cl.⁵ .......................................... G03B 29/00
[52] U.S. Cl. .................................... 354/62; 351/206
[58] Field of Search ............... 354/62; 351/205, 206, 351/207, 208

[56] References Cited

U.S. PATENT DOCUMENTS 4,666,268  5/1987  Ito ............................ 351/206

Primary Examiner—Michael L. Gellner
Assistant Examiner—Howard B. Blankenship
Attorney, Agent, or Firm—Finnegan, Henderson, Farabow, Garrett & Dunner

[57] ABSTRACT

This invention provides a photographic optical system for a fundus camera comprising an objective lens, a photographic diaphragm, a focusing lens, a field diaphragm and a relay lens adjacent to the subject's eye. In this system, the focusing lens has a positive power, and consequently a large aperture imaging lens can be avoided and the system made compact without adversely affecting optical performance.

3 Claims, 3 Drawing Sheets

FUNDUS CAMERA PHOTOGRAPHIC OPTICAL SYSTEM

FIELD OF THE INVENTION

This invention relates to the improvement of a photographic optical system for photographing the fundus of a subject's eye.

DESCRIPTION OF THE PRIOR ART

A fundus camera photographic optical system is known in the art comprising an objective lens 1, photographic diaphragm 2, focusing lens 3 and imaging lens 4 as shown schematically in FIG. 2.

The objective lens 1 is situated upfield of the subject's eye 5 at a predetermined working distance D. A first fundus image 7 of the fundus 6 of the subject's eye 5 is formed at a position M1 by the objective lens 1. If the power of the subject's eye 5 is ±0 diopter, light reflected from the fundus 6 emerges from the subject's eye 6 as a parallel light beam, impinges on the objective lens 1, and forms an image at the focal point of the objective lens 1.

FIG. 2 shows the case wherein the camera angle $2\alpha=45$ degrees.

If the image height of the first fundus image 7 is y1, the photographic diaphragm 2 is in a conjugate position to the pupil 8 of the subject's eye 5 with respect to the objective lens. The focusing lens 3 has a negative power, and the imaging lens 4 has a positive power.

The focusing lens 3 relays the first fundus image 7 from the position M1 to a position M2. At the position M2, a second fundus image 9 is formed as a virtual image by the focusing lens 3. Let the image height of this image 8 be y2. The focusing lens 3 has a negative power in order to shorten the length of the overall photographic optical system.

If the power of the subject's eye 5 changes, the position of the first fundus image 7 is displaced along the optic axis 01 depending on the power as shown by the arrow A. Now, if the position of the first fundus image 7 changes, a clear third fundus image 10 cannot be formed by the imaging lens 4 on a film 11 disposed at a position M3. The focusing lens 3 is therefore displaced along the optic axis 01 depending on the shift of this first image 7 so that the position M2 of the second fundus image 8 is maintained constant with respect to the imaging lens 4 regardless of the subject's eye 5. The position M2 of the second fundus image 8 is thus stabilized by displacing this focusing lens 3. A field diaphragm 12 is disposed immediately in front of the position M2.

The focal length f0 of the objective lens 1 lies in the range $40 \text{ mm} \leq f0 \leq 50 \text{ mm}$ due to the working distance D, the conjugate relationship between the pupil 8 of the subject's eye 5 and the photographic diaphragm 2, the overall length of the fundus camera and the positional relationship of the optical components. Here, it will be assumed that f0=45 mm.

At points close to the optic axis, the height y1 of the first fundus image 7 is given by $y1=f0\times\tan(\alpha/2)=45\tan(45/2)=18.6$ mm.

If the distance from the focal point of the objective lens 1 to the focusing lens 3 and the distance from the position M2 to the focusing lens 3 are the same (which means that the system functions as a relay without producing any magnification), the focusing lens 3 must be displaced by 1 mm when the position M1 is displaced by 1 mm. To reduce the displacement of the focusing lens 3, it is therefore preferable that the magnification $\beta1$ of the relay from the first fundus image 7 to the second fundus image 9 is less than 1, and particularly preferable that it is no greater than 0.5. Here, it will be assumed that this magnification is approx. 0.4.

If the film 11, which is the recording medium, is 35 mm film, the film is 24 mm high × 36 mm wide, so it is preferable that the diameter of the image is approx. 22 mm. In this case, if the height y3 of the third fundus image 10 is approx. y3=11 mm, the relay magnification $\beta$ from the position M1 to the position M8 is:

$$\beta=(y3/y1)=11/(-18.8)=0.6$$

If this relay magnification $\beta$ from the position M1 to the position M2 is $\beta1$, and the relay magnification from the position M2 to the position M3 is $\beta2$, $\beta$ may be expressed by:

$$\beta=\beta1\times\beta2$$

As the relay magnification $\beta1$ is (y2/y1), the relay magnification $\beta2$ is (y3/y2) and $\beta1=0.4$, we may write:

$$\beta=(y2/y1)\times(y3/y2)=0.4\times(-1.5)=-0.6$$

and it is therefore desirable that $\beta2=-1.5$.

Another fundus camera photographic system is known in the art which can record simultaneously on 35 mm film and a TV camera as shown schematically in FIG. 3.

This photographic optical system comprises a half mirror 13, field diaphragm 14, field lens 15, reflecting mirror 16, TV relay lens 17 and TV camera 18.

The film 11 and field diaphragm 14 are in conjugate positions with respect to the half mirror 13. Part of the light beam which forms a second fundus image 9 passes through the half mirror 13 so as to form an image on the film 11. The remaining light is reflected by the half mirror 13, and the second fundus image 9 is formed as a third fundus image 19 for TV at a position M4 where the field diaphragm 14 is situated. Let the height of this third fundus image 19 be y4, where y4=y3.

The field lens 15 is provided to efficiently collect light for the TV relay lens 17, while the reflecting mirror 18 is provided to make the whole apparatus more compact and make the number of reflections an even number. A fourth fundus image 21 is formed on the imaging surface 20 of the TV camera 18 (position M5).

If the TV camera 18 is ½ inch, the screen is 4.8 mm high × 6.4 mm wide. The image should therefore have a diameter of 4.4 mm, and the relay magnification $\beta TV$ of the TV relay lens 17 should be:

$$\beta TV=(2y5/2y4)=4.4/22=0.2$$

where the TV relay lens 17 has a positive power. Also, as the fourth fundus image 21 (height y5) is a real image of the third image 19 (height y4)), $\beta TV=-0.2$.

The overall relay magnification $\beta T$ from position M1 to position M5 is:
$$\beta T=(\beta1\times\beta2)\times\beta TV=(-0.6)\times(-0.2)=0.12$$

Photographic optical systems also exist wherein a dichroic mirror or a quick return mirror is used instead of the half mirror 13.

SUMMARY OF THE INVENTION

Conventional photographic optical systems were however designed mainly for 35 mm film. In these systems, insofar as concerns the imaging lens 4, light from peripheral object points passed mainly through the edge of the lens. Since the F number of the imaging lens 4 was large and the optical system was dark, a large aperture lens was required. To increase the aperture as many as 5 or 6 lenses were necessary, and the photographic optical system of the fundus camera became extremely complex.

It is therefore an object of the invention to provide a photographic optical system for a fundus camera wherein the imaging lens of large aperture is eliminated and the system is made more compact without sacrificing optical performance.

In order to achieve this object, the photographic optical system of this invention, which comprises an objective lens, a photographic diaphragm, a focusing lens, a field diaphragm and a relay lens arranged in that order away from the subject's eye, is characterized in that the focusing lens has a positive power.

The field diaphragm is disposed at the imaging point of the focusing lens which has the position of the fundus image formed by the objective lens as its object point.

The fundus image formed by the objective lens is relayed by the focusing lens, and this fundus image is relayed again by a relay lens. If the relay magnification of the focusing lens is $\beta1$, and the relay magnification of the relay lens is $\beta2$, the absolute values of both the relay magnification $\beta1$ and the relay magnification $\beta2$ are less than 1.

BRIEF DESCRIPTION OF THE ATTACHED DRAWINGS

DESCRIPTION OF THE PREFERRED EMBODIMENT

An embodiment of the photographic optical system for fundus cameras according to this invention will now be described with reference to drawings.

Figure 1:
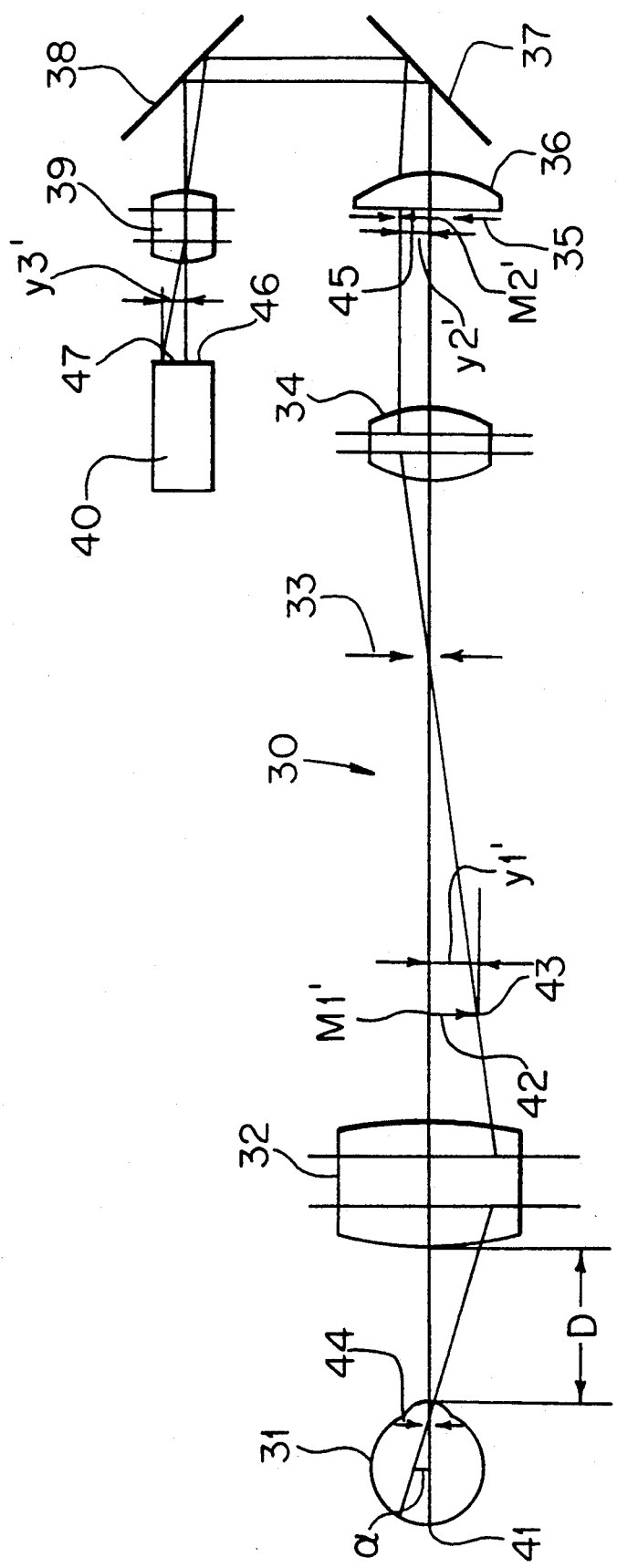
FIG. 1 is a schematic view of one embodiment of the photographic optical system of the fundus camera according to this invention.
Figure 2:
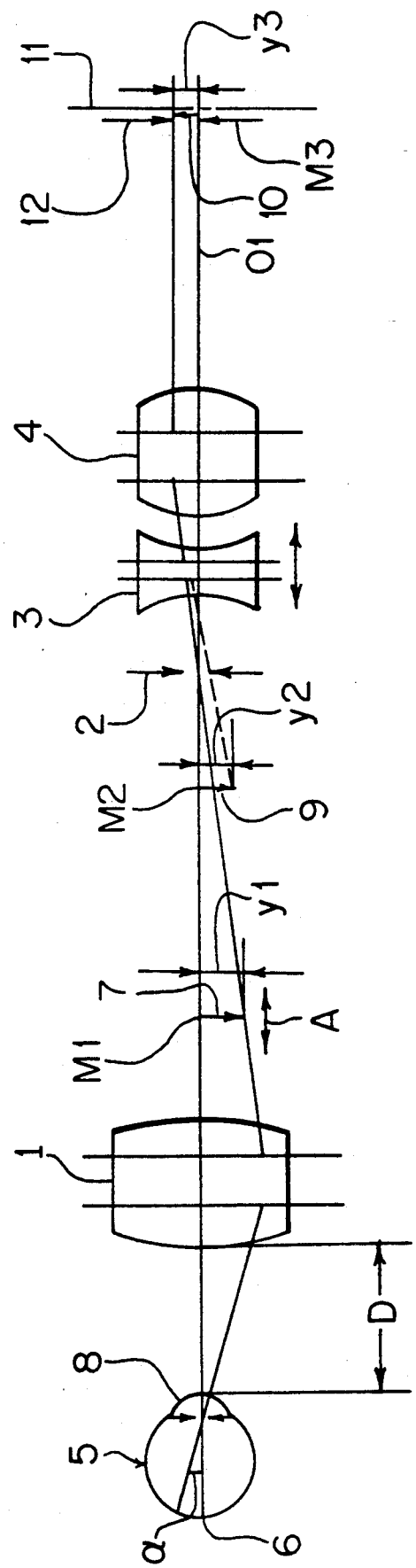
FIG. 2 is a schematic view of one type of photographic optical system in a conventional fundus camera.
Figure 3:
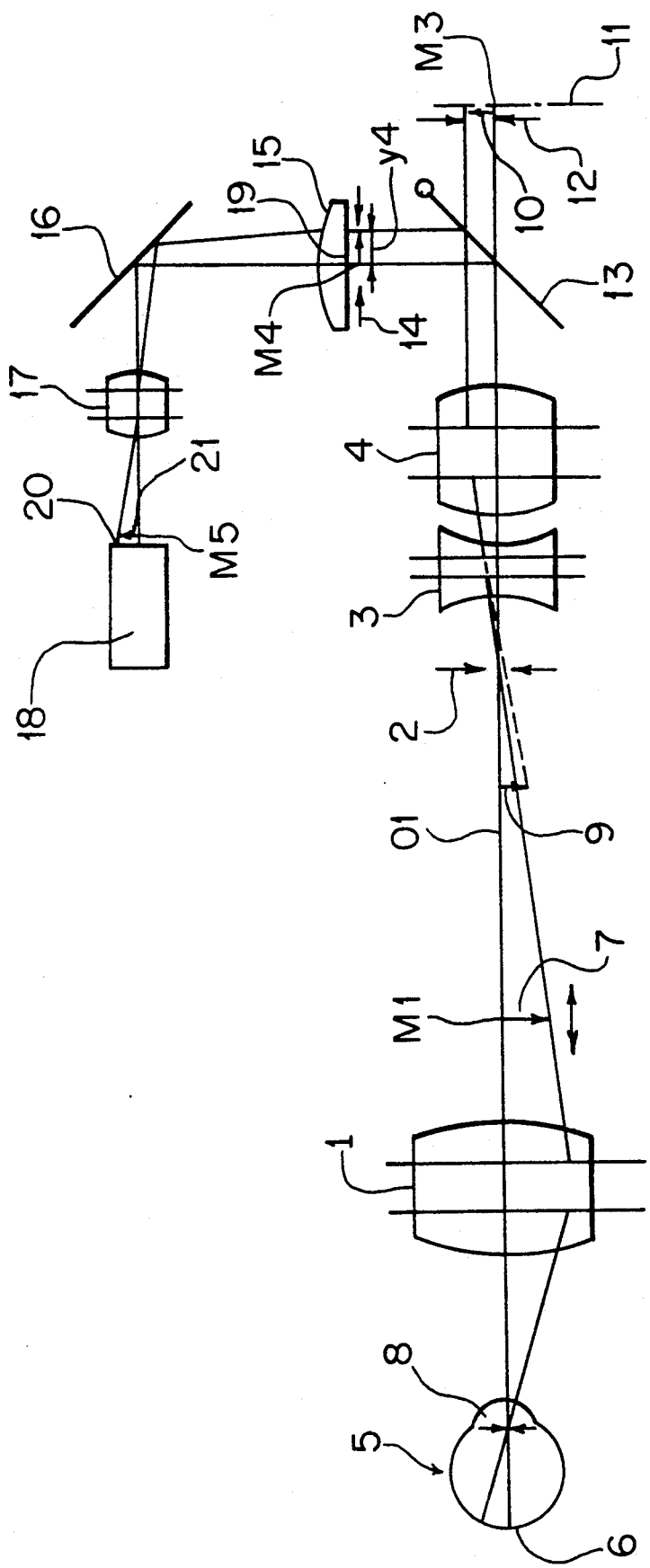
FIG. 3 is a schematic view of another type of photographic optical system in a conventional fundus camera.

In FIG. 1, 30 is a photographic optical system of a fundus camera. This photographic optical system 30 comprises a subject's eye 31, an objective lens 32 adjacent to the subject's eye 31, a photographic diaphragm 33, focusing lens 34, field diaphragm 35, field lens 36, reflecting mirrors 37, 38, TV relay lens 39 and TV camera 40.

The objective lens 32 is set at a predetermined working distance D in front of the subject's eye 31. This objective lens 32 is also used in an illuminating system, not shown, for illuminating the fundus 41 of the subject's eye 31. A first fundus image 42 is formed by this objective lens 32 at a position M1'. Let the height of this first fundus image 42 be y1'.

The photographic camera angle $2\alpha$ (=45 degrees), the focal length f0 of the objective lens 32 (=45 mm), the working distance D and the image height y1' are the same as in the conventional case.

The principal light beam which has passed through the apex 43 of the first fundus image 43, is led through the center of the photographic diaphragm 33 to the focusing lens 34.

The photographic diaphragm 33 and the pupil 44 of the subject's eye 31 are in conjugate positions with respect to the objective lens 32, the diaphragm 33 restricting the amount of light in the light beam forming the fundus image of the photographic optical system 30.

The focusing lens 34 has the role of relaying the first fundus image formed at the position M1' to the position M2' where the field diaphragm 35 is situated, and it has a positive power.

The field diaphragm 35 is disposed at a position M2', the imaging point of the focusing lens 34 which has the position M1' of the first fundus image as its object point.

A second fundus image 45 is formed as a real image at the position M2' by this focusing lens 34. Let the height of this second fundus image 45 be y2'.

The position M1' of the first fundus image 42 is displaced forwards or backwards along the optic axis depending on the power of the subject's eye 35. However, by displacing the focusing lens 34 along the optic axis, the position at which the second fundus image 45 is formed can be maintained at M2'.

The light beam which forms the second fundus image 45 is led via the field lens 36 and reflecting mirrors 37, 38 to the TV relay lens 39.

The field lens 38 has the role of efficiently condensing the light beam into the TV relay lens 39. The light beam forming the second fundus image 45 is brought by the TV relay lens 39 to an image at a position M3' which is the imaging surface 46 of the TV camera 40, and a third fundus image 47 is formed on this surface 46. Let the height of this third fundus image 47 be y3'.

If the screen size of the TV camera 40 is ½ inch as in the prior art, the image height y3' is 2.2 mm as in the conventional case.

As the height y1' of the first fundus image 42 is 18.6 mm and the height y3' of the third fundus image 47 is 2.2 mm, the overall relay magnification $\beta T$ of the photographic optical system 30 is y3'/y1'−0.12. The relay magnification $\beta 1$ of the focusing lens 34 is therefore −0.4 as in the prior art, and the relay magnification $\beta TV$ of the TV relay lens is −0.3.

If the TV camera 40 has a ⅔ inch screen, the screen is 8.8 mm high×8.8 mm wide. The image should then preferably have a diameter of approx. 6 mm. In this case, the overall relay magnification $\beta T$ of the photographic optical system 30 is given by:

$$\beta T = (8 \text{ mm}/18.8 \text{ mm}) = 0.16$$

and if the relay magnification $\beta 1$ is −0.4, $\beta TV = -0.4$.

If the TV camera 40 has a ⅓ inch screen, the screen is 3.3 mm high×4.4 mm wide. The image should then preferably have a diameter of approx. 3 mm. In this case, the overall relay magnification $\beta T$ of the photographic optical system 30 is given by:

$$\beta T - (1.5 \text{ mm}/18.6 \text{ mm}) = 0.08$$

and if the relay magnification $\beta 1$ is −0.4, $\beta TV = -0.2$.

If the photographic camera angle $\alpha$ is varied, a variable power lens, not shown, is inserted in the photographic optical system 30.

Further, by suitably setting the relay magnification $\beta 1$, the field lens 36 can be omitted.

In this invention, as described hereintofore, the focusing lens has a positive power. The imaging lens may therefore be omitted and the system made more compact without adversely affecting optical characteristics.

What is claimed is:

1. A photographic optical system for a fundus camera comprising an objective lens, a photographic diaphragm, a focusing lens, a field diaphragm and a relay lens arranged in that order away from the subject's eye, characterized in that said focusing lens has a positive power.

2. A photographic optical system for a fundus camera as defined according to claim 1, characterized in that said field diaphragm is disposed at the imaging point of the focusing lens having the position of the fundus image formed by the objective lens as its object point.

3. A photographic optical system for a fundus camera as defined according to claim 1, characterized in that the fundus image formed by said objective lens is relayed by said focusing lens, this fundus image then being relayed by said relay lens; and in that if the relay magnification of said focusing lens is $\beta 1$ and the relay magnification of said relay lens is $\beta 2$, the absolute values of both the relay magnification $\beta 1$ and the relay magnification $\beta 2$ are less than 1.

* * * * *